United States Patent [19]

Shin

[11] Patent Number: 5,330,980
[45] Date of Patent: Jul. 19, 1994

[54] MEDICAMENT FOR THE TOPICAL TREATMENT OF SKIN

[76] Inventor: Jae S. Shin, Kangnam-ku, Gaepo-Dong, Hyundai Apt. 203-905, Seoul, Rep. of Korea

[21] Appl. No.: 934,034

[22] Filed: Aug. 24, 1992

[51] Int. Cl.⁵ .................. A61K 31/655; A61K 31/10
[52] U.S. Cl. ..................................... 514/157; 514/709
[58] Field of Search .................. 514/709, 157

[56] References Cited

U.S. PATENT DOCUMENTS 3,761,590 9/1973 Fox ..................................... 424/228

OTHER PUBLICATIONS

Chemical Abstracts 115:197828y (1991).

Merck Index 11th ed #8947 (1989).

Primary Examiner—Marianne M. Cintins
Assistant Examiner—Kimberly R. Jordan
Attorney, Agent, or Firm—Ladas & Parry

[57] ABSTRACT

A medicament for the topical treatment of burned, irritated, ulcered, chafed, or infected, skin, a method of making the medicament, and a method of use of the medicament, the medicament comprising: about 70.6% by weight of Petrolatum U.S.P.(Vaseline); about 6.8% by weight of Wool Fat U.S.P.; about 4.0% by weight of a Sulfa compounded-ingredient; about 17.4% by weight of Zinc Oxide U.S.P.; and about 1.2% by weight of Disodium Formad Dehyde Sulfoxylate Diamino Diphenyl Sulfone.

18 Claims, No Drawings

MEDICAMENT FOR THE TOPICAL TREATMENT OF SKIN

BACKGROUND OF THE INVENTION

1. Field of the Invention

This invention relates to the field of medicines for the treatment of skin, and more particularly to a medicament for the topical treatment of burned, irritated, ulcered, chafed, or infected skin, a method of preparing the medicament, and a method of treating skin with the medicament.

2. Brief Discussion of the Prior Art

Medicines for the treatment of skin disorders and irritations are known. Obviously, different medicines are prescribed for different skin problems. In this description, however, for the sake of simplicity, and although not generic, the term "burned skin" will be used to mean burned, irritated, ulcered, chafed, or infected skin.

"Sofratulle", made by the French Pharmaceutical Company, Roussel, is one of the most popular medicines to treat burned skin. However, compared to Sofratulle, the medicine according to the present invention is conspicuous in at least three important aspects of skin medicine. First, the period of medical treatment is shortened to about one half of the treatment time needed with the application of Sofratulle. Secondly, the medicine of this invention results in the burned skin healing with minimum scarring as compared with Sofratulle. For example, proper treatment of second degree burned skin with the medicine of this invention will not leave any trace of scarring. Finally, the medicine according to the current invention is free from harmful side effects.

The present invention provides a medicament for the topical treatment of burned, irritated, ulcerated, chafed, or infected, skin, as well as a method of making the medicament, and a method of use of the medicament, the medicament comprising: about 36.0% to 85.3% by weight of petrolatum U.S.P. (Vaseline TM); about 3.4% to 13.6% by weight of wool fat U.S.P.; about 2% to 12% by weight of a sulfa compounded-ingredient; about 8.7% to 34.8% by weight of zinc oxide U.S.P.; and about 0.6% to 3.6% by weight of disodium formaldehyde sulphoxylate diaminodiphenyl sulfone.

Preferably, for best results, the medicament would be formulated to comprise: about 70.6% by weight of petrolatum U.S.P. (Vaseline TM); about 6.8% by weight of wool-fat U.S.P.; about 4.0% by weight of a sulfa compounded-ingredient; about 17.4% by weight of zinc oxide U.S.P.; and about 1.2% by weight of disodium formaldehyde sulphoxylate diaminodiphenyl sulfone. For the purposes of this description, and for convenience, the preferred proportions for the medicament will be used. However, it is to be understood that when such preferred portions are used, unless otherwise indicated, the ranges given above also apply.

The invention also includes a method of preparing the medicament comprising the steps of: admixing in a container, at room temperature (i.e. typically about 23° C.), about 70.6% by weight of petrolatum U.S.P. (Vaseline TM), about 6.8% by weight of wool-fat U.S.P., about 4.0% by weight of a sulfa compounded-ingredient, about 17.4% by weight of zinc oxide U.S.P., and about 1.2% by weight of disodium formaldehyde sulphoxylate diaminodiphenyl sulfone; stirring the mixture for about 30 minutes; raising temperature, if needed, to within the range of 25° C. to 40° C.; stirring the mixture again for about 30 minutes at the elevated temperature until there are no residues or lumps of powdered ingredients; and allowing the mixture to return to room temperature.

The invention additionally includes a method of treatment skin irritations comprising the steps of: a) removing visible tiny stones and dirt possibly with sanitary cotton but not with a disinfectant; b) lancing any blisters on the skin surface; c) preparing a bandage dressing by depositing on it an effective amount of the medicament (for example, by liberally coating the bandage to produce a thin 1 to 3 mm layer of the medicament above the surface of the bandage and having an area at least equal to that of the damaged skin); d) applying the bandage dressing to the affected skin area, covering the bandage dressing with a layer of cotton, swathing the bandaged skin area if possible, and leaving the bandage in place for about 48 hours; e) removing the bandage; f) lancing any new blisters; g) dabbing the skin area with cotton balls if the area is watery, but not cleaning with a disinfectant; and h) repeating steps c. through g. until the skin is healed.

Because the medicament works as an effective disinfectant, cleaning the skin area is essentially not necessary, and other types of disinfectant should not be applied to the skin area.

A bandage dressing containing an amount of the medicament which has been applied to liberally coat the bandage to produce a thin 1 to 3 mm layer of the medicament above the surface of the bandage is another aspect of the invention.

Preferably, the sulfa compounded-ingredient is selected from the group consisting sulphadiazine, sulphacetamide, sulphamerazine, sulphamezathine, and sulphanilamide.

A typical batch mixture of ingredients comprising the medicament is as follows: about 14.60 mg of petrolatum U.S.P.(Vaseline TM); about 1.40 mg of wool-fat U.S.P.; about 0.84 mg of Sulfa Diazin U.S.P.; about 3.60 mg of zinc oxide U.S.P.; and about 0.25 mg of disodium formaldehyde sulphoxylate diaminodiphenyl sulfone.

The preferred temperature for the admixing and first stirring steps in the method of preparing the medicament as noted above is room temperature, i.e. about 23° C. in a typical controlled environment room, while the second stirring step is preferably performed at an elevated temperature of about 40° C., so as to completely admix the ingredients more effectively by melting them.

DETAILED DESCRIPTION OF THE PREFERRED EMBODIMENT

The chemical makeup and nature of each ingredient of the medicament according to this invention will be understood to be defined by the similar terms found in the *United States Pharmacopeia* (U.S.P.), describing drugs, chemicals, and medicinal preparations.

In the preparation of the medicament, the ingredients, petrolatum (14.60 mg), wool-fat (1.40 mg), Sulfa Diazin (0.84 mg), zinc oxide (3.60 mg), and disodium formaldehyde sulphoxylate diaminodiphenyl sulfone (0.25 mg), are put in a bowl, and the temperature is raised, if necessary, to room temperature or above, and preferably in the range of 18° C. to 30° C. The ingredients are then admixed by stirring well for approximately 30 minutes.

The mixture is then recommended to be heated to within the temperature range of 25° C. to 40° C., and preferably 40° C., and is again stirred well for approximately 30 minutes so that no residues or tiny lumps of powdered ingredients are evident in the mixture.

The mixture is then allowed to come to room temperature either before or after being packaged for distribution (in jars, dispensing tubes, or the like).

The medicine of this invention has been found to be effective in the healing of a number of skin disorders, including burned skin, posttraumatic ulcers, varicose ulcers, diabetic ulcers, decubitic, pyogenesis, congelation (frostbite) ulcers, diaper exanthema, and skin infections following burns or skin ulcers.

In use, assuming as an example the treatment of burned skin, the area of skin requiring treatment is not required to be cleaned, except for removal of any visible tiny stones and dirt, and the rough removal of any other previously applied medication. A disinfectant should not be used. If blisters are evident, they are to be lanced prior to application of the medicine.

The proper size of gauze or bandage is then selected, preferably folded about four times for a suitable thickness, and an amount of the medicament is applied to cover the bandage with a thin layer using a spreader such as a knife. The layer of medicament should be thick enough so as not to soak into the bandage and should be of an area adequate to cover the area of the damaged skin. On skin without blisters, the medicated bandage dressing thus prepared is applied and covered with a layer of cotton which is then secured with an outer bandage, tape, or other appropriate means, while an outer bandage is recommended.

This bandage is left on the burned skin for approximately 48 hours. After 48 hours, the bandage is clipped with scissors and removed all at once. If the burn is a third degree or worse burn, there may be some yellow smelly pus on the surface of the skin. This is considered a normal condition.

Any visible tiny stones or dirt should again be removed with sanitary cotton balls, but the skin should not be cleaned with a disinfectant. The prior-applied medication left on the skin is not necessary to be thoroughly removed.

If there are blisters in the affected area, they should be lanced.

Again, the appropriate size bandage dressing is selected, and the subsequent steps set forth above are repeated until the skin is healed.

A test of the need for additional medication will be evident by the presence of water or moist medicament when the bandage is removed. When no water or moisture is found on the skin and the medication is dry, the treatment is finished.

For about one week after healing, soap should not be used for cleaning the healed skin area. Also, during the week after healing, the patient should avoid direct sunlight on the affected skin area.

If the burn is a second degree burn or below, it has been found that three applications of the medication will properly heal the skin. If over a second degree burn is being treated, it is not unusual to require three to five or more applications depending on how deeply the skin is damaged.

At the end of treatment, an itching sensation may occur, but this is a normal condition. However, the patient should be instructed not to scratch the affected area. If itching is extreme, then a dry bandage should be applied while sleeping.

The method for the treatment of skin disorders or irritations other than that described above in connection with burned skin is exactly the same, i.e. the treatment is continued until no water or moisture under the removed bandage is found. Just prior to applying a new bandage prepared with medicament, if the skin area is watery, the affected area is dabbed with cotton balls to remove as much water as possible.

For each ingredient of the medicament, a variation by approximately ±1% of the proportional amount would be permissible without detracting from the effectiveness of the medicine. Less effective results will be realized outside this tight range, and, for whatever reason different proportions are desired, the ranges given at the beginning of the above SUMMARY OF THE INVENTION may be used. However, accurate proportions as listed above are fairly recommended. The inventor invented the claimed medicine through research and experimental data. More than one hundred patients have been treated, and most of them, approximately 95%, have been successfully cured with full satisfaction. Because the medicine of the invention is based primarily on experimental data from clinical trials, formal test results are not available.

It will be apparent that modifications of the invention may come to mind, once the basic ingredients and effectiveness of the medicament has been understood and proven, without departing from the spirit and scope of the invention. Accordingly, the invention is not to be interpreted as being limited to the specific composition, method of preparation, and method of use as specified herein, but rather by the scope of the appended claims.

I claim:

1. A medication for the topical treatment of burned, irritated, ulcered, chafed, or infected skin, comprising:
   a. about 36.0% to 85.3% by weight of petrolatum U.S.P.;
   b. about 3.4% to 13.6% by weight of wool-fat U.S.P.;
   c. about 2.0% to 12.0% by weight of a sulfa compounded-ingredient selected from the group consisting of sulphadiazine, sulphacetamide, sulphamerazine, sulphamezathine, and sulphanilamide;
   d. about 8.7% to 34.8% by weight of zinc oxide U.S.P.; and
   e. about 0.6% to 3.6% by weight of disodium formaldehyde sulphoxylate diaminodiphenyl sulfone.

2. A medication for the topical treatment of burned, irritated, ulcered, chafed, or infected skin, comprising:
   a. about 70.6% by weight of petrolatum U.S.P.;
   b. about 6.8% by weight of wool-fat U.S.P.;
   c. about 4.0% by eight of a sulfa compounded-ingredient selected from the group consisting of sulphadiazine, sulphacetamide, sulphamerazine, sulphamezathine, and sulphanilamide;
   d. about 17.4% by weight of zinc oxide U.S.P.; and
   e. about 1.2% by weight of disodium formaldehyde sulphoxylate diaminodiphenyl sulfone.

3. The medication as claimed in claim 1, wherein a typical mixture of ingredients comprises:
   a. about 14.60 mg. of petrolatum U.S.P.;
   b. about 1.3 mg. of wool-fat U.S.P.;
   c. about 0.84 mg. of sulphadiazine;
   d. about 3.60 mg. of zinc oxide U.S.P.; and
   e. about 0.25 mg. of disodium formaldehyde sulphoxylate diaminodiphenyl sulfone.

4. A method of preparing a medication for the topical treatment of burned, irritated, ulcered, chafed, or infected skin, comprising the steps of:

admixing in a container, at room temperature, about 70.6% by weight of petrolatum U.S.P., about 6.8% by weight of wool-fat U.S.P., about 4.0% by weight of a sulfa compounded-ingredient selected from the group consisting of sulphadiazine, sulphacetamide, sulphamerazine, sulphamezathine, and sulphanilamide, about 17.4% by weight of zinc oxide U.S.P., and about 1.2% by weight of disodium formaldehyde sulphoxylate diaminodiphenyl sulfone;

stirring the mixture for about 30 minutes;

raising temperature, to within the range of 25° C. to 40° C.;

stirring the mixture again for about 30 minutes at the elevated temperature until there are no residues or lumps of powdered ingredients; and allowing the mixture to return to room temperature.

5. The method as claimed in claim 4, wherein said second stirring step is performed at a temperature of about 40° C.

6. A method of treating skin disorders or irritations comprising the steps of:
  a. removing any visible tiny stones and dirt with sanitary cotton but not with a disinfectant;
  b. lancing any blisters on the skin surface;
  c. preparing a bandage dressing by depositing on it an effective amount of the medicament as claimed in claim 1;
  d. applying the bandage dressing to the affected skin area, covering with a layer of cotton, swathing the bandaged wound, and leaving the bandage in place for about 48 hours;
  e. removing the bandage and inspecting the skin;
  f. lancing any new blisters;
  g. removing traces of old medication with sanitary cotton by simply dabbing the skin area; and
  h. repeating steps c. through g. until skin is healed.

7. The method as claimed in claim 6, wherein the skin disorder or irritation is burned skin.

8. The method as claimed in claim 6, wherein the skin disorder or irritation is posttraumatic ulcerated skin.

9. The method as claimed in claim 6, wherein the skin disorder or irritation is varicose ulcerated skin.

10. The method as claimed in claim 6, wherein the skin disorder or irritation is diabetic ulcerated skin.

11. The method as claimed in claim 6, wherein the skin disorder or irritation is a decubitus ulcer.

12. The method as claimed in claim 6, wherein the skin disorder or irritation is pyogenic.

13. The method as claimed in claim 6, wherein the skin disorder or irritation is abscessed skin.

14. The method as claimed in claim 6, wherein the skin disorder or irritation is frostbite ulcerated skin.

15. The method as claimed in claim 6, wherein the skin disorder or irritation is diaper exanthem.

16. The method as claimed in claim 6, wherein the skin disorder or irritation is a skin infection subsequent to being subjected to burns or skin ulcers.

17. A bandage dressing for application to the skin in the treatment of skin disorders or irritations, comprising:

a bandage or gauze upon which an effective amount of the medicament as claimed in claim 1 is deposited, said effective amount being such as to form a thin layer of the medicament to a thickness sufficient to give 48 hours of lasting effect of the medicament.

18. The bandage dressing as claimed in claim 17, wherein said thickness of medicament is 1 to 3 mm.

* * * * *